(12) United States Patent
Jensen et al.

(10) Patent No.: US 8,216,220 B2
(45) Date of Patent: Jul. 10, 2012

(54) SYSTEM AND METHOD FOR TRANSMISSION OF COMBINED DATA STREAM

(75) Inventors: Jeffrey L. Jensen, Boulder, CO (US); Mark B. Savage, Superior, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 1329 days.

(21) Appl. No.: 11/899,759

(22) Filed: Sep. 7, 2007

(65) Prior Publication Data

US 2009/0069801 A1    Mar. 12, 2009

(51) Int. Cl.
*A61B 18/10* (2006.01)
(52) U.S. Cl. .......... 606/34; 375/238; 375/239; 375/295
(58) Field of Classification Search .............. 606/34, 606/41; 375/238, 239, 295
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |

(Continued)

FOREIGN PATENT DOCUMENTS

DE    179607    3/1905

(Continued)

OTHER PUBLICATIONS

International Search Report EP 06010499.9 dated Jan. 29, 2008.

(Continued)

*Primary Examiner* — Michael Peffley
*Assistant Examiner* — Daniel Fowler

(57) ABSTRACT

An electrosurgical system is disclosed. The electrosurgical system includes an electrosurgical instrument configured to generate a first and second data streams and a transmission circuit configured to convert the first and second data streams into a pulsed transmission signal. The first signal property of the transmission signal is representative of the first data stream and the second signal property of the transmission signal is representative of the second data stream. The transmission circuit is further configured to process the transmission signal to decode the first signal property into the first data stream and the second signal property into the second data stream.

11 Claims, 4 Drawing Sheets

U.S. PATENT DOCUMENTS

| | | |
|---|---|---|
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,580,575 A * | 4/1986 | Birnbaum et al. ............ 600/484 |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A * | 2/1990 | Stasz et al. ................ 606/37 |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,067,953 A | 11/1991 | Feucht |
| 5,075,839 A | 12/1991 | Fisher et al. |
| 5,087,257 A | 2/1992 | Farin |
| 5,099,840 A | 3/1992 | Goble et al. |
| 5,103,804 A | 4/1992 | Abele et al. |
| 5,108,389 A | 4/1992 | Cosmescu |

| Patent | Type | Date | Inventor |
|---|---|---|---|
| 5,108,391 | A | 4/1992 | Flachenecker |
| 5,119,284 | A | 6/1992 | Fisher et al. |
| 5,122,137 | A | 6/1992 | Lennox |
| 5,133,711 | A | 7/1992 | Hagen |
| 5,151,102 | A | 9/1992 | Kamiyama et al. |
| 5,152,762 | A | 10/1992 | McElhenney |
| 5,157,603 | A | 10/1992 | Scheller et al. |
| 5,160,334 | A | 11/1992 | Billings et al. |
| 5,161,893 | A | 11/1992 | Shigezawa et al. |
| 5,167,658 | A | 12/1992 | Ensslin |
| 5,167,659 | A | 12/1992 | Ohtomo et al. |
| 5,190,517 | A | 3/1993 | Zieve et al. |
| 5,196,008 | A | 3/1993 | Kuenecke |
| 5,196,009 | A | 3/1993 | Kirwan, Jr. |
| 5,201,900 | A | 4/1993 | Nardella |
| 5,207,691 | A | 5/1993 | Nardella |
| 5,230,623 | A | 7/1993 | Guthrie et al. |
| 5,233,515 | A | 8/1993 | Cosman |
| 5,234,427 | A | 8/1993 | Ohtomo et al. |
| 5,249,121 | A | 9/1993 | Baum et al. |
| 5,249,585 | A | 10/1993 | Turner et al. |
| 5,254,117 | A | 10/1993 | Rigby et al. |
| RE34,432 | E | 11/1993 | Bertrand |
| 5,267,994 | A | 12/1993 | Gentelia et al. |
| 5,267,997 | A | 12/1993 | Farin |
| 5,281,213 | A | 1/1994 | Milder et al. |
| 5,282,840 | A | 2/1994 | Hudrlik |
| 5,290,283 | A | 3/1994 | Suda |
| 5,295,857 | A | 3/1994 | Toly |
| 5,300,068 | A | 4/1994 | Rosar et al. |
| 5,300,070 | A | 4/1994 | Gentelia |
| 5,304,917 | A | 4/1994 | Somerville |
| 5,318,563 | A | 6/1994 | Malis et al. |
| 5,323,778 | A | 6/1994 | Kandarpa et al. |
| 5,324,283 | A | 6/1994 | Heckele |
| 5,330,518 | A | 7/1994 | Neilson et al. |
| 5,334,183 | A | 8/1994 | Wuchinich |
| 5,334,193 | A | 8/1994 | Nardella |
| 5,341,807 | A | 8/1994 | Nardella |
| 5,342,356 | A | 8/1994 | Ellman |
| 5,342,357 | A | 8/1994 | Nardella |
| 5,342,409 | A | 8/1994 | Mullett |
| 5,346,406 | A | 9/1994 | Hoffman et al. |
| 5,346,491 | A | 9/1994 | Oertli |
| 5,348,554 | A | 9/1994 | Imran et al. |
| 5,370,645 | A | 12/1994 | Klicek et al. |
| 5,370,672 | A | 12/1994 | Fowler et al. |
| 5,370,675 | A | 12/1994 | Edwards et al. |
| 5,372,596 | A | 12/1994 | Klicek et al. |
| 5,383,874 | A | 1/1995 | Jackson |
| 5,383,876 | A | 1/1995 | Nardella |
| 5,383,917 | A | 1/1995 | Desai et al. |
| 5,385,148 | A | 1/1995 | Lesh et al. |
| 5,400,267 | A | 3/1995 | Denen et al. |
| 5,403,311 | A | 4/1995 | Abele et al. |
| 5,403,312 | A | 4/1995 | Yates et al. |
| 5,409,000 | A | 4/1995 | Imran |
| 5,409,485 | A | 4/1995 | Suda |
| 5,413,573 | A | 5/1995 | Koivukangas |
| 5,414,238 | A | 5/1995 | Steigerwald et al. |
| 5,417,719 | A | 5/1995 | Hull et al. |
| 5,422,567 | A | 6/1995 | Matsunaga |
| 5,422,926 | A | 6/1995 | Smith et al. |
| 5,423,808 | A | 6/1995 | Edwards et al. |
| 5,423,809 | A | 6/1995 | Klicek |
| 5,423,810 | A | 6/1995 | Goble et al. |
| 5,423,811 | A | 6/1995 | Imran et al. |
| 5,425,704 | A | 6/1995 | Sakurai et al. |
| 5,429,596 | A | 7/1995 | Arias et al. |
| 5,430,434 | A | 7/1995 | Lederer et al. |
| 5,432,459 | A | 7/1995 | Thompson |
| 5,433,739 | A | 7/1995 | Sluijter et al. |
| 5,436,566 | A | 7/1995 | Thompson |
| 5,438,302 | A | 8/1995 | Goble |
| 5,443,463 | A | 8/1995 | Stern et al. |
| 5,445,635 | A | 8/1995 | Denen |
| 5,451,224 | A | 9/1995 | Goble et al. |
| 5,452,725 | A | 9/1995 | Martenson |
| 5,454,809 | A | 10/1995 | Janssen |
| 5,458,597 | A | 10/1995 | Edwards et al. |
| 5,462,521 | A | 10/1995 | Brucker et al. |
| 5,472,441 | A | 12/1995 | Edwards et al. |
| 5,472,443 | A | 12/1995 | Cordis et al. |
| 5,474,464 | A | 12/1995 | Drewnicki |
| 5,480,399 | A | 1/1996 | Hebborn |
| 5,483,952 | A | 1/1996 | Aranyi |
| 5,496,312 | A | 3/1996 | Klicek |
| 5,496,313 | A | 3/1996 | Gentelia et al. |
| 5,496,314 | A | 3/1996 | Eggers |
| 5,500,012 | A | 3/1996 | Brucker et al. |
| 5,500,616 | A | 3/1996 | Ochi |
| 5,511,993 | A | 4/1996 | Yamada et al. |
| 5,514,129 | A | 5/1996 | Smith |
| 5,520,684 | A | 5/1996 | Imran |
| 5,531,774 | A | 7/1996 | Schulman et al. |
| 5,534,018 | A | 7/1996 | Wahlstrand et al. |
| 5,536,267 | A | 7/1996 | Edwards et al. |
| 5,540,677 | A | 7/1996 | Sinofsky |
| 5,540,681 | A | 7/1996 | Strul et al. |
| 5,540,682 | A | 7/1996 | Gardner et al. |
| 5,540,683 | A | 7/1996 | Ichikawa |
| 5,540,684 | A | 7/1996 | Hassler, Jr. |
| 5,541,376 | A | 7/1996 | Ladtkow et al. |
| 5,545,161 | A | 8/1996 | Imran |
| 5,556,396 | A | 9/1996 | Cohen et al. |
| 5,558,671 | A | 9/1996 | Yates |
| 5,562,720 | A | 10/1996 | Stern et al. |
| 5,569,242 | A | 10/1996 | Lax et al. |
| 5,571,147 | A | 11/1996 | Sluijter et al. |
| 5,573,533 | A | 11/1996 | Strul |
| 5,584,830 | A | 12/1996 | Ladd et al. |
| 5,588,432 | A | 12/1996 | Crowley |
| 5,596,466 | A | 1/1997 | Ochi |
| 5,599,344 | A | 2/1997 | Paterson |
| 5,599,345 | A | 2/1997 | Edwards et al. |
| 5,599,348 | A | 2/1997 | Gentelia et al. |
| 5,605,150 | A | 2/1997 | Radons et al. |
| 5,609,560 | A | 3/1997 | Ichikawa et al. |
| 5,613,966 | A | 3/1997 | Makower et al. |
| 5,620,481 | A | 4/1997 | Desai et al. |
| 5,626,575 | A | 5/1997 | Crenner |
| 5,628,745 | A | 5/1997 | Bek |
| 5,628,771 | A | 5/1997 | Mizukawa et al. |
| 5,643,330 | A | 7/1997 | Holsheimer et al. |
| 5,647,869 | A | 7/1997 | Goble et al. |
| 5,647,871 | A | 7/1997 | Levine et al. |
| 5,651,780 | A | 7/1997 | Jackson et al. |
| 5,658,322 | A | 8/1997 | Fleming |
| 5,660,567 | A | 8/1997 | Nierlich et al. |
| 5,664,953 | A | 9/1997 | Reylek |
| 5,674,217 | A | 10/1997 | Wahlstrom et al. |
| 5,675,609 | A * | 10/1997 | Johnson ................ 375/237 |
| 5,678,568 | A | 10/1997 | Uchikubo et al. |
| 5,681,307 | A | 10/1997 | McMahan |
| 5,685,840 | A | 11/1997 | Schechter et al. |
| 5,688,267 | A | 11/1997 | Panescu et al. |
| 5,693,042 | A | 12/1997 | Boiarski et al. |
| 5,693,078 | A | 12/1997 | Desai et al. |
| 5,694,304 | A | 12/1997 | Telefus et al. |
| 5,695,494 | A | 12/1997 | Becker |
| 5,696,441 | A | 12/1997 | Mak et al. |
| 5,697,925 | A | 12/1997 | Taylor |
| 5,697,927 | A | 12/1997 | Imran et al. |
| 5,702,386 | A | 12/1997 | Stern et al. |
| 5,702,429 | A | 12/1997 | King |
| 5,707,369 | A | 1/1998 | Vaitekunas et al. |
| 5,712,772 | A | 1/1998 | Telefus et al. |
| 5,713,896 | A | 2/1998 | Nardella |
| 5,718,246 | A | 2/1998 | Vona |
| 5,720,742 | A | 2/1998 | Zacharias |
| 5,720,744 | A | 2/1998 | Eggleston et al. |
| 5,722,975 | A | 3/1998 | Edwards et al. |
| 5,729,448 | A | 3/1998 | Haynie et al. |
| 5,733,281 | A | 3/1998 | Nardella |
| 5,735,846 | A | 4/1998 | Panescu et al. |
| 5,738,683 | A | 4/1998 | Osypka |
| 5,743,900 | A | 4/1998 | Hara |
| 5,743,903 | A | 4/1998 | Stern et al. |

| Patent | Date | Inventor |
|---|---|---|
| 5,749,869 A | 5/1998 | Lindenmeier et al. |
| 5,749,871 A | 5/1998 | Hood et al. |
| 5,755,715 A | 5/1998 | Stern |
| 5,766,153 A | 6/1998 | Eggers et al. |
| 5,766,165 A | 6/1998 | Gentelia et al. |
| 5,769,847 A | 6/1998 | Panescu |
| 5,772,659 A | 6/1998 | Becker et al. |
| 5,788,688 A | 8/1998 | Bauer et al. |
| 5,792,138 A | 8/1998 | Shipp |
| 5,797,902 A | 8/1998 | Netherly |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Bussey et al. |
| 5,830,212 A | 11/1998 | Cartmell |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,959,253 A | 9/1999 | Shinchi |
| 5,961,344 A | 10/1999 | Rosales et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 5,999,848 A | 12/1999 | Gord et al. |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,093,186 A | 7/2000 | Goble |
| 6,102,497 A | 8/2000 | Ehr et al. |
| 6,102,907 A | 8/2000 | Smethers et al. |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven |
| 6,123,701 A | 9/2000 | Nezhat |
| 6,123,702 A | 9/2000 | Swanson et al. |
| 6,132,429 A | 10/2000 | Baker |
| 6,142,992 A | 11/2000 | Cheng et al. |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,171,304 B1 | 1/2001 | Netherly et al. |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,259,937 B1 | 7/2001 | Schulman |
| 6,261,285 B1 | 7/2001 | Novak |
| 6,261,286 B1 | 7/2001 | Goble et al. |
| 6,267,760 B1 | 7/2001 | Swanson |
| 6,273,886 B1 | 8/2001 | Edwards |
| 6,275,786 B1 | 8/2001 | Daners |
| 6,293,941 B1 | 9/2001 | Strul |
| 6,293,942 B1 | 9/2001 | Goble et al. |
| 6,293,943 B1 | 9/2001 | Panescu et al. |
| 6,296,636 B1 | 10/2001 | Cheng et al. |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards |
| 6,364,877 B1 | 4/2002 | Goble et al. |
| 6,371,963 B1 | 4/2002 | Nishtala et al. |
| 6,383,183 B1 | 5/2002 | Sekino et al. |
| 6,387,092 B1 * | 5/2002 | Burnside et al. ............... 606/32 |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |

| | | |
|---|---|---|
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,890,331 B2 | 5/2005 | Kristensen |
| 6,893,435 B2 | 5/2005 | Roane |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |

| Patent No. | Date | Inventor |
|---|---|---|
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,525,398 B2 | 4/2009 | Nishimura et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |
| 2003/0120271 A1 | 6/2003 | Burnside |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Fleming |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek et al. |
| 2004/0193021 A1 | 9/2004 | Zdeblick |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0004634 A1 | 1/2005 | Ricart et al. |
| 2005/0021020 A1 | 1/2005 | Blaha et al. |
| 2005/0021022 A1 | 1/2005 | Sturm et al. |
| 2005/0101949 A1 | 5/2005 | Harano et al. |
| 2005/0101951 A1 | 5/2005 | Wham |
| 2005/0109111 A1 | 5/2005 | Manlove |
| 2005/0109935 A1 | 5/2005 | Manlove |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2006/0291178 A1 | 12/2006 | Shih |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |

| | | |
|---|---|---|
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1707144 | 3/2006 |
| EP | 1645235 | 4/2006 |
| EP | 880220 | 6/2006 |
| EP | 1707143 | 10/2006 |
| EP | 1744354 | 1/2007 |
| EP | 1810628 | 7/2007 |
| EP | 1810630 | 7/2007 |
| EP | 1810633 | 7/2007 |
| EP | 1854423 | 11/2007 |
| FR | 1275415 | 10/1961 |
| FR | 1347865 | 11/1963 |
| FR | 23137013 | 12/1976 |
| FR | 2364469 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO95/25471 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO 9912607 | 3/1999 |
| WO | WO02/00129 | 1/2002 |
| WO | WO 0200129 | 1/2002 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/043240 | 5/2004 |
| WO | WO2004/052182 | 6/2004 |
| WO | WO 2004052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060365 | 7/2005 |
| WO | WO2005/060849 | 7/2005 |
| WO | WO2006/050888 | 5/2006 |
| WO | WO2006/105121 | 10/2006 |

OTHER PUBLICATIONS

International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 Dec. 20, 2007.
International Search Report EP 07019174.7 dated Jan. 29, 2008.
International Search Report EP08015601.1, Dated: Dec. 5, 2008.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297, Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Muller et al. "Extended Left Hemicolectomy Using the LigaSure Vessel Sealing System" Innovations That Work; Sep. 1999.
International Search Report PCT/US03/37110 dated Jul. 25, 2010.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 05002769.7 dated Jun. 9, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001527.6 dated May 9, 2007.
International Search Report EP 07004355.9 dated May 21, 2007.
International Search Report EP 07008207.8 dated Sep. 5, 2007.
International Search Report EP 07010673.7 dated Sep. 24, 2007.
European Search Report for European Application No. 11182150.0 dated Nov. 3, 2011.
US 6,878,148, 04/2005, Goble et al. (withdrawn)

* cited by examiner

SYSTEM AND METHOD FOR TRANSMISSION OF COMBINED DATA STREAM

BACKGROUND

1. Technical Field

The present disclosure relates to electrosurgical apparatuses, systems and methods. More particularly, the present disclosure is directed to a system and method of transmitting data from an electrosurgical device to an electrosurgical generator, wherein the data includes a plurality of data streams.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

Ablation is most commonly a monopolar procedure that is particularly useful in the field of cancer treatment, where one or more RF ablation needle electrodes (usually of elongated cylindrical geometry) are inserted into a living body. A typical form of such needle electrodes incorporates an insulated sheath from which an exposed (uninsulated) tip extends. When an RF energy is provided between the return electrode and the inserted ablation electrode, RF current flows from the needle electrode through the body. Typically, the current density is very high near the tip of the needle electrode, which tends to heat and destroy surrounding tissue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

To perform the above-described electrosurgical procedures, various types of electrosurgical devices having specific electrode configurations are used. Generally, these electrosurgical devices include a variety of input controls and are configured to communicate with an electrosurgical generator. However, conventional electrosurgical instruments and generators utilize complicated circuits and processes for transmitting and receiving data which greatly limits functionality of these devices.

SUMMARY

The present disclosure relates to a system and method for transmitting multiple data streams relating to an electrosurgical instrument via a single pulsed transmission signal. First and second data streams are encoded into a signal transmission signal and transmitted across an isolation barrier to a signal processor, wherein the frequency of the transmission signal is representative of the first data stream and the pulse width is representative of the second data stream. The signal processor includes circuitry configured to decode the transmission signal to obtain the first and second data stream. More particularly, the signal processor includes a pulse counter for measuring the number of pulses of the transmission signal and a pulse width converter for measuring the pulse width of the transmission signal to obtain the first and second data streams, respectively.

According to one aspect of the present disclosure, an electrosurgical system is disclosed. The electrosurgical system includes an electrosurgical instrument configured to generate a first and second data streams and a transmission circuit configured to convert the first and second data streams into a pulsed transmission signal. First signal property of the transmission signal is representative of the first data stream and second signal property of the transmission signal is representative of the second data stream. The transmission circuit is further configured to process the transmission signal to decode the first signal property into the first data stream and the second signal property into the second data stream.

The present disclosure also relates to a method for the transmission of data which includes the steps of generating a first and second data streams and converting the first and second data streams into a pulsed transmission signal, wherein a first signal property of the transmission signal is representative of the first data stream and a second signal property of the transmission signal is representative of the second data stream. The method also includes the step of processing the transmission signal to decode the first signal property into the first data stream and the second signal property into the second data stream.

According to another aspect of the present disclosure, a data transmission system is disclosed. The system includes a transmission circuit configured to convert the first and second data streams into a pulsed transmission signal. The first signal property of the transmission signal is representative of the first data stream and the second signal property of the transmission signal is representative of the second data stream. The transmission circuit is further configured to process the transmission signal to decode the first signal property into the first data stream and the second signal property into the second data stream.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
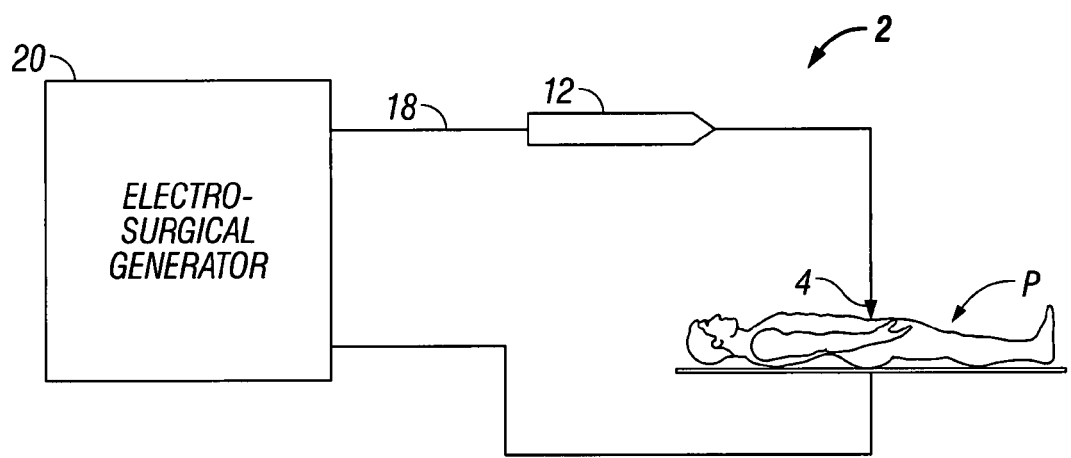
FIG. 1 is a schematic block diagram of an electrosurgical system according to the present disclosure.

FIG. 1 is a schematic illustration of an electrosurgical system according to one embodiment of the present disclosure. The system includes an electrosurgical instrument 2 having a hand piece 12 and one or more electrodes 4 for treating tissue of a patient P. The instrument 2 may be a monopolar or bipolar instrument including one or more active electrodes (e.g., electrosurgical cutting probe, ablation electrode(s), sealing forceps, etc.).

The hand piece 12 is connected to the generator 10 by a cable 18 which includes a plurality of wires for transmitting electrical energy, hereinafter a supply line. Electrosurgical RF energy is supplied to the instrument 2 by a generator 20 via the supply line, allowing the instrument 2 to coagulate, seal, ablate and/or otherwise treat tissue. During electrosurgery the energy is returned to the generator 20 through a return electrode (not specifically shown). In a monopolar system, the return electrode is a conductive pad attached to the patient. In a bipolar system, wherein the instrument 2 is a bipolar electrosurgical forceps having opposing jaw members which include the active electrode 4 and a return electrode (not specifically shown) disposed therein, electrosurgical energy is similarly returned through the return electrode.

The generator 20 includes input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, tissue sealing, intensity setting, etc.).

Figure 2:
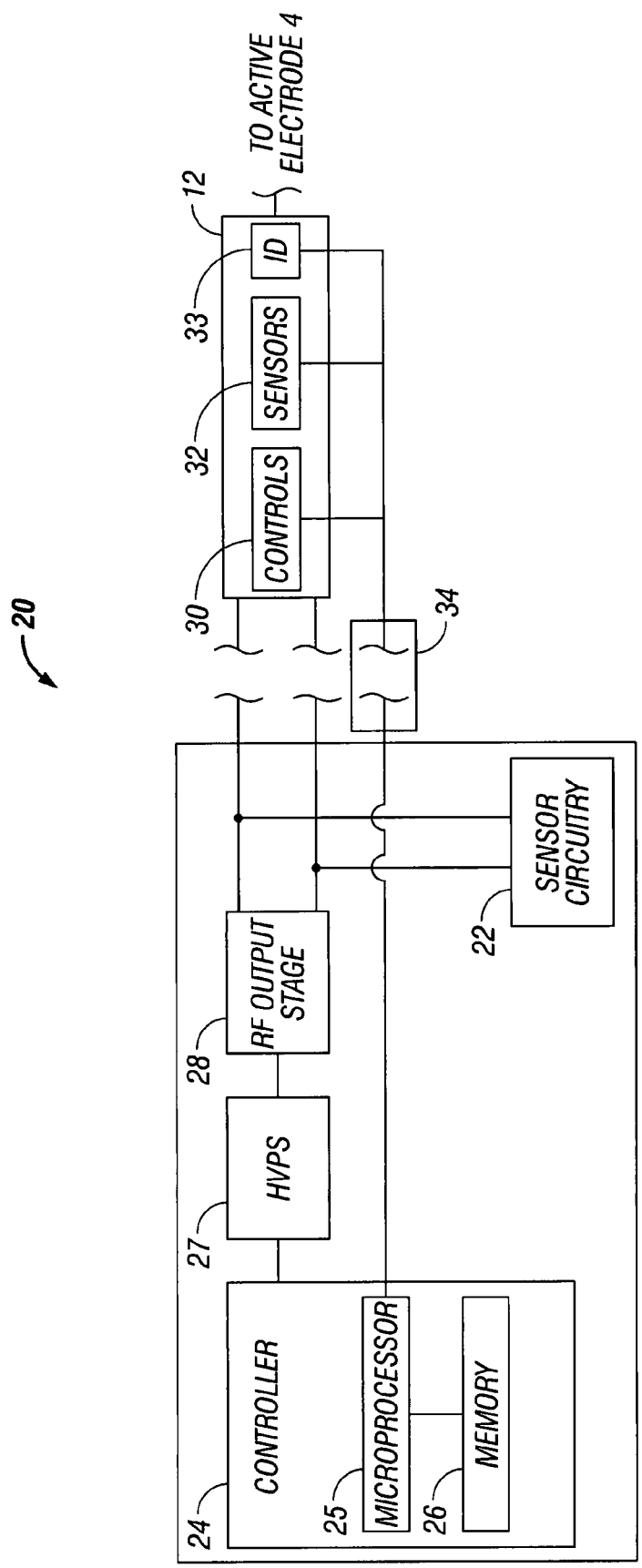
FIG. 2 is a schematic block diagram of a generator and a hand piece according to one embodiment of the present disclosure.
Figure 3:
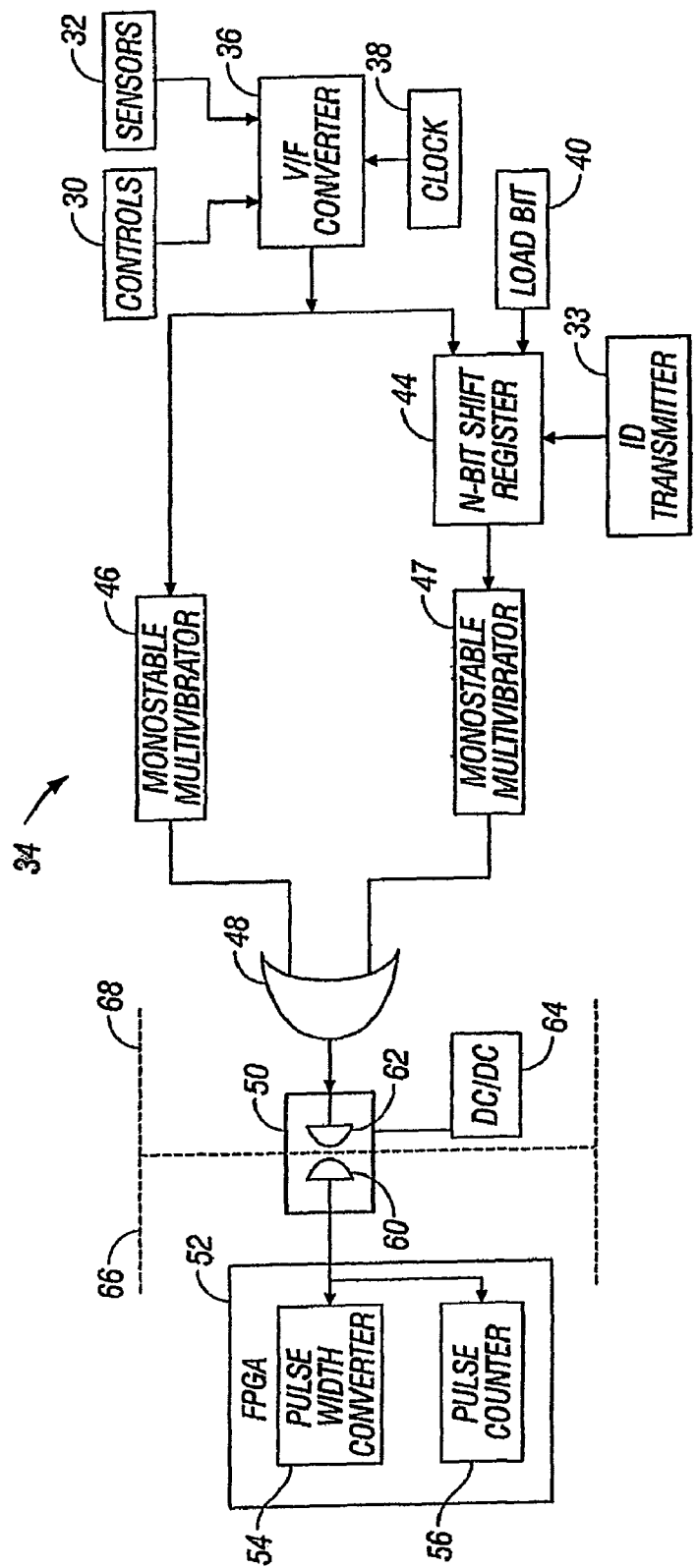
FIG. 3 is an schematic block diagram of a transmission circuit according to the present disclosure.

FIG. 2 shows a schematic block diagram of the generator 20 and the hand piece 12. The generator 20 includes a controller 24, a high voltage DC power supply 27 ("HVPS") and an RF output stage 28. The HVPS 27 is connected to a conventional AC source (e.g., electrical wall outlet) and provides high voltage DC power to an RF output stage 28 which then converts high voltage DC power into RF energy and delivers the RF energy to the active terminal 30. The energy is returned thereto via the return terminal 32.

In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

The generator 20 may include a plurality of connectors to accommodate various types of electrosurgical instruments (e.g., monopolar instruments, electrosurgical forceps, etc.). Further, the generator 20 is configured to operate in a variety of modes such as ablation, monopolar and bipolar cutting coagulation, etc. It is envisioned that the generator 20 may include a switching mechanism (e.g., relays) to switch the supply of RF energy between the connectors, such that, for instance, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop wherein sensor circuit 22, which may include a plurality of sensors measuring a variety of tissue and energy properties (e.g., tissue impedance, tissue temperature, output current and/or voltage, etc.), provides feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

The hand piece 12 includes one or more input controls 30 (FIG. 2) to adjust certain operating parameters of the generator 20, sensors 32 and ID transmitter 33. Placing the input controls at the instrument 2 allows for easier and faster modification of RF energy parameters during the surgical procedure without requiring interaction with the generator 20. The controls 30 include a plurality of input devices (e.g., buttons, switches, etc.) for adjusting intensity of the electrosurgical energy and selecting the operating mode (e.g., cut, coagulation, blend). The controls 30 provide complementary and/or redundant controls for the generator 20 which may be used to adjust the intensity of the energy output by the generator, change the operating mode (e.g., cut, coagulate, blend). The controls 30 include a plurality of resistive elements coupled to the inputs so that the inputs correspond to specific resistances. This allows for fewer wires to be used within the controls 30 since different input signals (e.g., corresponding voltage) can be transmitted along a single wire by varying the resistance thereby varying the voltage of the control current. The controls 30 transmit control signals to the generator 20.

DC voltage is employed by the hand piece 12 to transmit input signals to the generator 20. The DC voltage may be supplied by a DC power source via a DC line of the cable 18. More specifically, a DC voltage source is used to transmit a control current which is used by the hand piece 12 to transmit input signals to the generator 10. Using DC voltage to transmit control signals is well known in the art and is described in commonly owned U.S. Pat. Nos. 3,699,967 and 3,801,800, both of which are hereby incorporated by reference in their entirety herein.

The sensor 32 may include temperature sensors, impedance sensors, etc. which are in electrical communication with the active electrode 4 and are configured to measure tissue and/or energy properties at the treatment site. During operation, the sensors 32 transmit sensor signals to the microprocessor 25 and/or sensor circuitry 22.

The ID transmitter 33 stores and transmits an n-bits unique integer which serves as an identifier for the hand piece 12. This allows the generator 20 to identify which hand piece 12 is transmitting the sensor and/or control signals. Identifying the hand piece 12 is particularly important in electrosurgical procedures utilizing multiple active electrodes, such as ablation procedures, wherein multiple electrodes are used to ablate a wide segment of tissue. During such procedures, it is desirable to monitor tissue and energy properties for each of the active electrodes 14. This allows the generator 20 to pair the sensor and control signals with the corresponding hand piece 12 based on the transmitted identifier.

A transmission circuit 34 connects the controls 30, the sensors 32 and ID transmitter 33 of the hand piece 12 to the microprocessor 25. The transmission circuit 34 is configured to combine multiple data streams into a single pulsed transmission signal. The pulsed transmission signal includes a stream of pulses, the frequency of which represents a first data stream. The first data stream may be a voltage signal representative of some quantity of interest. The width of pulses of the pulsed transmission signal represents a second data stream, which denotes a second quantity of interest. The first and second data streams could be continuous analog signal levels, a sequence of digital logic levels, and the like. The first data stream may be either control signals or the sensor signals transmitted by the controls 30 and sensors 32, respectively, and the second data stream may be the identifier signal transmitted by the ID transmitter 33.

The controls 30 and sensors 32 are connected to a voltage-to-frequency converter 36 and transmit the control and sensor signals, respectively, thereto. The control and sensor signals, e.g., first data stream, are voltage signals and are converted to corresponding frequency pulses at the V/F converter 36. The V/F converter 36 transmits the frequency pulses to a first monostable multivibrator 46, wherein upon receiving the frequency pulse, the first multivibrator 46 creates a first pulsed signal having a fixed pulse length as a function of the frequency pulse of the V/S converter 36.

The V/F converter 36 is also coupled to a clock 28 which generates a clock signal at a predetermined frequency, such as 1 MHz. In response to the 1 MHz clock signal, the V/F converter 36 also transmits the frequency pulses to a n-bit shift register 44. The n-bit shift register 44 is a parallel-in serial-out shift register which is configured to output either a "1" or a "0" in response to the clocked signal from the V/F converter 36. In particular, the shift register 44 outputs serial data and accepts parallel digital data as input, with each parallel data bit appearing at the output in succession. After each parallel data bit has appeared at the output, the sequence begins again.

The shift register 44 is configured to accept parallel inputs from a load bit 40 and the ID transmitter 33, which provides the identifier, e.g., second data stream, for the hand piece 12 thereto. The shift register 44 is connected to a monostable multivibrator 47 which outputs pulses based on the input from the shift register 44. If the shift register 44 outputs a logic high (e.g., "1") the multivibrator 47 outputs a second pulsed signal having a pulse wider than the first pulsed signal of the V/F converter 36. If the shift register 44 outputs a "0" the multivibrator 47 does not create a second pulsed signal.

The first pulsed signal of the V/F converter 36 and the second pulsed signal passing through the multibirator 47 are "OR-ed" at a digital logic two-input NOR gate 48 and the longer of the two pulsed signals is output therethrough thereby forming the pulsed transmission signal. The NOR gate 48 combines the pulses of the first pulsed signal from the first multivibrator 46, which are of variable time period (e.g., frequency) but of fixed pulse width, with the pulses of the second pulsed signal from the second multivibrator 47 which are also of fixed width to generate a pulsed transmission signal. The transmission signal includes pulses of variable time period/frequency and variable pulse width.

More specifically, the first pulsed signal is combined with the second pulsed signal, from the first and second multivibrators 46, 47 respectively, at the NOR gate 48. The first pulsed signal drives one input of the NOR gate 48 and causes the output of the NOR gate to a logic low "e.g., "0") state, regardless of the state of the second input of the NOR gate 48. If the shift register 44 causes the multivibrator 47 to output the second pulsed signal, which is thereafter is transmitted to a digital logic two-input NOR gate 48, the second pulse drives the second input of the NOR gate 48 and forces the output of the NOR gate 48 to a logic low ("0") state as well, regardless of the state of the first input to the NOR gate driven by the V/F converter 36.

Values of the RC networks (e.g, V/F converter 36, shift register 44, etc.) connected to the multivibrators 46, 47 are set such that the length of the pulse created by the second multivibrator 47 is longer than the length of the pulse created by the first multivibrator 46. This allows for detection processing of the output pulses from the NOR gate 48 to distinguish between so called "short" and so called "long" pulses, and thus determine whether the bit from the shift register 44 is a logic low ("0") due to a short pulse or a logic high ("1") due to a longer pulse. The timing of the longer pulse is also set by the components of the RC network such that the maximum length of a long pulse is less than the minimum pulse period from the V/F converter 36 driving the first multivibrator 46.

The output of the NOR gate 48 is driven low ("0") when the output of either of the multivibrators 46, 47 is logic high ("1"). If the first multivibrator creates a short output pulse, and the second multivibrator 47 creates no output pulse, the output of the NOR gate remains low ("0") only for the duration of the short pulse from the first multivibrator 46. Since the output of the shift register 44 controls the pulse output of the second multivibrator 47, the length of the output pulse from the NOR gate 48, e.g., the pulsed transmission signal, corresponds to the logic state output of the shift register 44 driving the second multivibrator 47.

The pulsed transmission signal is passed through an isolation barrier 50 which connects a non-isolated portion 66 (e.g., generator 20) with an isolated portion 68 (e.g., hand piece 12). The isolation barrier 50 includes one or more optical couplers 60 on the non-isolated portion 66 and one or more corresponding optical couplers 62 on the isolated portion 68. The optical couplers 60, 62 transmit the pulsed transmission signal across a physical gap, thereby isolating the hand piece 12 from the generator 20. In addition to optical couplers 60, 62 or similar light emitting devices, the isolation barrier 50 includes converters, such as analog-to-digital, digital-to-analog, voltage-to-frequency and frequency-to-voltage converters. Power is provided to the isolated portion optical couplers via an isolated DC/DC converter 64. Those skilled in the art will understand that the isolated DC/DC converter 64 and the isolation barrier 50 are optional if isolation is not desired.

The pulsed transmission signal is then passed through the isolation barrier to a signal processor (e.g., field programmable gate array 52) at the non-isolated portion 66. The frequency or the time period represented by the pulsed transmission signal is variable from pulse to pulse. The detection of the value of interest in the pulsed transmission stream is accomplished by one of the following: measuring the interval of time between pulses to obtain the pulse time period or counting the number of pulses received over some fixed interval of time, to obtain the average frequency of the pulsed transmission signal and thereby decode the first data stream. The width of each pulse is measured simultaneously with the frequency of the pulses of the pulsed transmission to extract the successive value of each pulse and thereby form the second data stream.

The signal processor measures both the time period/frequency and width of the pulses of the pulsed transmission signal to detect the first and second data streams, respectively. The signal processor uses digital logic wherein one counter is used to measure the pulse period or frequency and a second counter is used to measure the pulse width of each individual pulse. Those skilled in the art will appreciate that various counting circuits may be used to perform the detection function of the signal processor.

More specifically, the FPGA 52 decodes the pulsed transmission signal to obtain voltage information (e.g., pulse counts per unit of time) representative of the first data stream (e.g., control or sensor signals) and pulse width information representative of the second data steam (e.g., ID information). In particular, the FPGA 52 includes a pulse width converter 54 which measures the width of pulses of the pulsed transmission signal and then converts the pulse width to the hand piece 12 ID information. The FPGA 52 also includes a pulse counter 56 which decodes sensor or control signals by counting the number of pulses of the signal (e.g., frequency thereof). The decoded information is thereafter transmitted to the microprocessor 25 wherein the microprocessor 25 takes corresponding actions (e.g., adjust power, output ID information, etc.).

In one embodiment, the counter 56 counts the pulse width to distinguish between low ("0") and high ("1") logic states. In another embodiment, the counter 56 can be expanded to multiple logic level depending on resolution thereof to represent multiple bits. In particular, the binary logic level discussed above encompasses two (e.g., $2^1$) states, which is sufficient to represent two pulsed signals encoding two data streams. Using a higher logic level which encompasses four (e.g., $2^2$) or more (e.g., $2^n$) states allows to represent multiple pulsed signals encoding multiple data streams. For instance, four pulse width represented by "00" "01" "10" and "11" may be used to describe four pulse states representative of four data streams.

The non-isolated portion 66, namely the generator 20 provides a signal which synchronizes the loading of the data inputs to the shift register 44 with the edges of the pulses from the V/F converter 36 to control the output order of the shift register 44. Since the generator 20 controls the timing of the loading of the bits into the shift register 44, the generator 20 can extract the register bits from the width of the pulses in the second data stream in the same sequence as the bits are output from the shift register 44.

In another embodiment, loading of the inputs to the shift register 44 can be performed entirely by the isolated portion 68 thereby alleviating the need for a load signal from the generator 20 to synchronize the data. This further reduces the need for signals to cross the isolation barrier 50.

This may be accomplished by transmitting a so-called "preamble" signal in addition to the data bits for the data streams to allow data detection circuitry (e.g., FPGA 52) on the non-isolated portion 66 to synchronize with the data stream transmitted by the circuitry (e.g., the NOR gate 48) on the isolation portion 68. The preamble is a unique bit pattern of 1's and 0's that does not duplicate nay of the possible bit patterns that occur in the data streams. The preamble is generated by encoding the N beats of the second data stream into a larger number of M bits. Since not all $2^M$ bit patterns are required to transmit the $2^N$ possible combinations of the bits in the second data stream, a unique pattern of M bits can be used as the preamble data pattern as illustrated below:

| | |
|---|---|
| Second data stream having 8 bits: | 1 1 1 1 1 1 1 1 |
| Second data stream encoded to 10 bits: | 0 1 0 1 1 1 1 1 1 1 |
| Preamble data, 10 bits: | 1 0 1 0 1 0 1 0 1 0 |
| Transmitted data sequence, 20 bits: | 1 0 1 0 1 0 1 0 1 0 0 1 0 1 1 1 1 1 1 1 |

The FPGA 22 which detects the second data stream can then synchronize to the second data stream by waiting until the preamble pattern is detected. Once the preamble pattern is detected, the remaining bits in the data stream represent the data bits for the second data stream.

Figure 4:
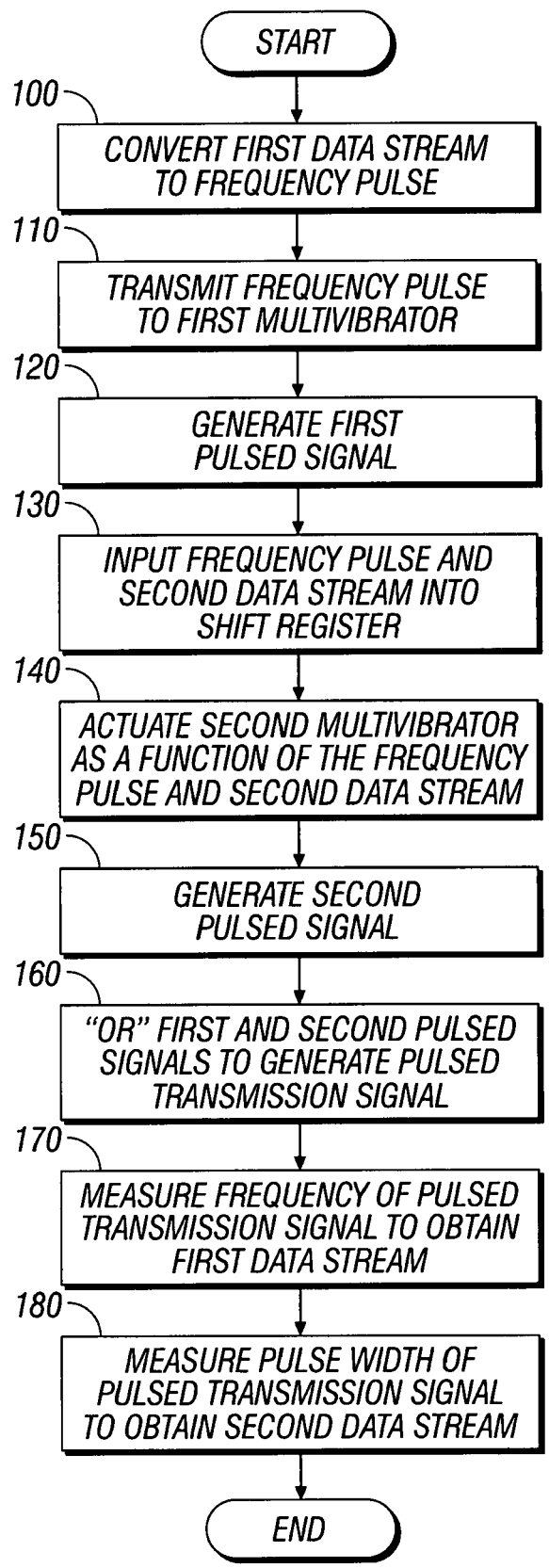
FIG. 4 is a flow chart illustrating a method for transmission for combined data streams according to the present disclosure.

FIG. 4 illustrates a method for transmission of the first and second data stream via a single pulsed transmission signal. In step 100, the first data stream, e.g. control and/or sensor signals, are converted to a frequency pulse by the V/F converter 36. The V/F converter 36 transmits the frequency pulse to the first multivibrator 46 in step 110. In step 120, the first multivibrator 46, in response to the frequency pulse generates the first pulsed signal.

In response to the clock 38, the V/F converter 36 also transmits the frequency pulse to the shift register 44. In step 130, the shift register 44 accepts the input of the frequency pulse and the ID data from the ID transmitter 33 and outputs either a logic high ("1") or low ("0"). In step 140, the second multivibrator 47 is actuated if the shift register 44 outputs a logic high and in step 150, the second multivibrator 47 generates a second pulsed signal which is longer than the first pulsed signal. In embodiments, more than two data streams may be transmitted via a single transmission signal by using higher logic states as discussed above.

In step 160, the first and second pulsed signals are processed at the NOR gate 48, wherein the longer of the pulses is used to form the pulsed transmission signal. The transmission signal is sent to the FPGA 52 across the isolation barrier 50. In step 170, the pulse counter 56 counts the number of pulses of the transmission signal to obtain the frequency and/or time period thereof and convert the obtained value into the first data stream. In step 180, the pulse width converter 54 measures the width of the pulses of the transmission signals to obtain the second data stream. The first and second data streams are thereafter transmitted to the microprocessor 25 for further processing.

The present disclosure provides for a system and method of combining two data stream for transmission using a single signal across an isolation barrier. Utilizing a single transmission signal minimizes the circuit complexity and power requirements of the isolated portion since the number of optical couplers or other isolated signal transmission components are reduced.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
   an electro surgical instrument configured to generate first and second data streams; and
   a transmission circuit configured to convert the first and second data streams into a pulsed transmission signal, wherein a first signal property of the transmission signal being representative of the first data stream and a second signal property of the transmission signal being representative of the second data stream, the transmission circuit further configured to process the transmission signal to decode the first signal property into the first data stream and the second signal property into the second data stream, wherein the transmission circuit includes:

a voltage-to-frequency converter to convert the first data stream into a corresponding first frequency pulse;

a first multivibrator for outputting a first pulsed signal in response to the first frequency pulse;

a shift register configured to accept as input the first frequency pulse and the second data stream and to output at least one of a high logic and a low logic signals;

a second multivibrator configured to output a second pulsed signal if the shift register outputs the high logic signal; and a NOR gate configured to select one of the first and second pulsed signals to form the transmission signal.

2. An electrosurgical system according to claim 1, wherein the electrosurgical instrument includes:

input controls configured to generate control signals which control an electrosurgical generator; and sensors configured to measure at least one of an energy property and a tissue property and generate sensor signals representative thereof.

3. An electrosurgical system according to claim 2, wherein the first data stream is selected from the group consisting of control signals and sensor signals.

4. An electrosurgical system according to claim 2, wherein the second data stream is an identifier for the electrosurgical instrument.

5. An electrosurgical system according to claim 1, wherein the first signal property is a frequency of the transmission signal.

6. An electrosurgical system according to claim 5, wherein the transmission circuit includes:

a pulse counter configured to measure the number of pulses of the transmission signal to determine the frequency thereof.

7. An electro surgical system according to claim 1, wherein the second signal property is a pulse width of each of the pulses of the transmission signal.

8. An electrosurgical system according to claim 7, wherein the transmission circuit includes:

a pulse width converter configured to measure the width of each of the pulses of the transmission signal.

9. A data transmission system comprising:

a transmission circuit configured to convert a first data stream and a second data stream into a pulsed transmission signal, wherein a first signal property of the transmission signal being representative of the first data stream and a second signal property of the transmission signal being representative of the second data stream, the transmission circuit is further configured to process the transmission signal to decode the first signal property into the first data stream and the second signal property into the second data stream; and wherein the transmission circuit includes;

a voltage-to-frequency converter to convert the first data stream into a corresponding first frequency pulse;

a first multivibrator for outputting a first pulsed signal in response to the first frequency pulse;

a shift register configured to accept as input the first frequency pulse and the second data stream and to output at least one of a high logic and a low logic signals;

a second multivibrator configured to output a second pulsed signal if the shift register outputs the high logic signal; and a NOR gate configured to select one of the first and second pulsed signals to form the transmission signal.

10. A data transmission system according to claim 9, wherein the first signal property is a frequency transmission signal and the second signal property is a pulse width of each of the pulses of the transmission signal.

11. A data transmission system according to claim 10, wherein the transmission circuit includes:

a signal processor configured to measure the width of each of the pulses of the transmission signal and number of pulses of the transmission signal to determine the frequency thereof.

* * * * *